United States Patent [19]
Chiao et al.

[11] Patent Number: 5,471,878
[45] Date of Patent: Dec. 5, 1995

[54] METHOD OF SUPPRESSING GRAIN NOISE IN ULTRASONIC WAVEFORM DATA BY 3D FILTERING

[75] Inventors: Richard Y. Chiao, Clifton Park, N.Y.; Patrick J. Howard, Cincinnati, Ohio

[73] Assignee: General Electric Company, Schenectady, N.Y.

[21] Appl. No.: 126,629

[22] Filed: Sep. 27, 1993

[51] Int. Cl.$^6$ .................................................. G01N 29/00
[52] U.S. Cl. ........................... 73/602; 382/141; 348/619
[58] Field of Search ............................. 73/602, 598, 618, 73/620, 606, 613, 629, 633; 382/54; 348/618, 619

[56] References Cited

U.S. PATENT DOCUMENTS

| | | | |
|---|---|---|---|
| 4,675,532 | 6/1987 | Carson | 358/209 |
| 4,750,367 | 6/1988 | Bernatets | 73/602 |
| 4,887,306 | 12/1989 | Hwang et al. | 382/54 |

OTHER PUBLICATIONS

"Digital Image Processing", Gonzalez et al, 1992, pp. 189–195.

Primary Examiner—Robert Raevis
Assistant Examiner—Nashmiya Ashraf
Attorney, Agent, or Firm—David C. Goldman; Paul R. Webb, II

[57] ABSTRACT

A method of suppressing grain noise resulting from ultrasonic inspection of an object, including ultrasonically scanning an object and detecting waveform signals therefrom, determining, from the signals, data values which define a 3D waveform data set $U(x,y,t)$ having both spatial $(x,y)$ and temporal $(t)$ ultrasonic data values from the scanned object, converting the 3D waveform data set into a 3D filtered waveform data set $V(x,y,t)$ by performing a 3D filtering operation thereon, wherein for each data value in the 3D waveform data set $U(x,y,t)$, a filtered data value is obtained by taking into account data values which are adjacent thereto both spatially and temporally, thereby reducing grain noise relative to flaw signals to enable a high probability of flaw detection and a low probability of false flaw indications.

31 Claims, 4 Drawing Sheets

METHOD OF SUPPRESSING GRAIN NOISE IN ULTRASONIC WAVEFORM DATA BY 3D FILTERING

BACKGROUND OF THE INVENTION

The present invention relates to the field of Ultrasonic inspection, and more particularly to a method of reducing grain noise in ultrasonic waveform data sets by three-dimensional (3D) filtering.

Ultrasonic pulse-echo inspection of titanium and other large grain metal objects is plagued by grain noise produced by ultrasonic reflections from large grain interfaces. Grain noise occurs because the microstructure of metals such as titanium or the like can be coarse which causes the grains of the microstructure to return signals during a raster scan of the object with an ultrasonic transducer. Due to the extruding and forging processes used in forming titanium parts, grain structure, and therefore grain noise, can vary significantly between different regions of an object. Grain noise can typically vary between 6–20 dB. The grains of the microstructure can produce echo signals during scanning of an object that can mask or conceal flaw indications in a defective region or produce false indications of flaws in defect free regions. False flaw indications can result in a defect-free part being rejected for use in an application. Masked flaw indications can result in the unintentional use of a defective part. Obviously, either masked flaw indications or false flaw indications can result in significant waste of time and materials in the manufacture of metal parts and/or an undesirable increased risk of part failure.

Ultrasonic inspection is typically used to inspect large metal rotating parts such as billets prior to forging, sonic shapes after forging, and machined parts such as engine fan disks or the like.

Typically, flaws in metal parts have a smaller spatial extent than the ultrasound illuminated grains of the metal microstructure. Thus, depending on the calibration of an ultrasonic data acquisition system used in scanning the object, flaw or signal correlation in the waveform data set collected therewith can be significantly greater, temporally and spatially, than the temporal and spatial correlation of the grain noise in the data set.

BRIEF DESCRIPTION OF THE PRIOR ART

In ultrasonic pulse echo inspection, a data acquisition system is employed to scan an object of interest and collect echo signals therefrom. The echo signals can be collected and digitized in a manner which produces waveform data, known as an A-scan, for each particular location of interest in the scanned object. Thus, data can be collected in ultrasonic inspection in a manner which produces a 3D waveform data set, sometimes referred to in the art as a T-scan or Z-scan, and which includes an A-scan for each location (x,y) in an area of interest on the object.

The individual waveforms or A-scans are then used to determine if flaws exist in the scanned object by looking for significant variations of the amplitude in the waveforms. Since grain noise may cause significant variations of the amplitude in the waveforms, it can be difficult to distinguish grain noise from flaw indications, particularly if the flaw indications have low temporal correlation through the waveform. Thus, flaw decisions which are independently based on the individual A-scans, respectively, can result in masked flaw indications or false flaw indications.

One-dimensional (1D) order-statistic filtering has been used on single waveforms in the past in an attempt to smooth out noise in waveforms. However, since flaw indications may not have high temporal correlation, 1D filtering has had limited success in flaw detection.

Two-dimensional (2D) filtering has previously been used on images to reduce noise. 2D median filtering has been used in video image processing with some success in reducing salt-and-pepper noise or noise having low spatial correlation.

A major disadvantage of the prior art is that it does not provide a method of flaw detection which takes advantage of the difference in both spatial and temporal correlations between flaws and grain noise in 3D ultrasonic waveform data sets. Thus, the prior art does not provide a method of flaw detection which maximizes the probability of flaw detection and minimizes the probability of false flaw indications.

SUMMARY OF THE INVENTION

A primary object of the invention is to provide an improved method for ultrasonic inspection of an object which enables a greater probability of flaw detection and less probability of false flaw indications than has heretofore been achieved with prior art inspection techniques.

Another object of the present invention is to provide a method for suppressing grain noise in ultrasonic inspection of an object, and to thereby enable a high probability of flaw detection and a low probability of false flaw indications.

A more specific object of the present invention is to provide a method for suppressing grain noise in ultrasonic inspection of an object which method advantageously uses the difference between grain noise correlation and a signal or flaw correlation in the object to promote accurate flaw detection.

A further object of the invention is to provide a method for suppressing grain noise in ultrasonic inspection of an object which method advantageously uses both the differences in noise and signal spatial correlations and noise and signal temporal correlations to promote flaw detection.

Another object of the invention is to provide a method for suppressing grain noise in ultrasonic inspection of an object which method provides a fast and effective method for selectively reducing grain noise without reducing flaw indications in a 3D waveform data set.

These and other objects and advantages are achieved by the present invention which provides a method of suppressing grain noise resulting from ultrasonic inspection of an object, including the steps of ultrasonically scanning an object and detecting waveform signals therefrom, determining, from the signals, data values which define a 3D waveform data set $U(x,y,t)$ having both spatial $(x,y)$ and temporal $(t)$ ultrasonic data values from the scanned object, converting the 3D waveform data set into a 3D filtered waveform data set $V(x,y,t)$ by performing a 3D filtering operation thereon, wherein for each data value in said 3D waveform data set $U(x,y,t)$, a filtered data value is obtained by taking into account data values which are adjacent thereto both spatially and temporally.

In accordance with one aspect of the invention, the step of scanning the object includes spatially sampling the object such that data values in the 3D waveform data set representing flaws in the object have a greater spatial correlation than data values representing grain noise in the 3D waveform data set.

In accordance with another aspect of the invention, the step of determining data values includes sampling the waveform signals such that data values in the 3D waveform data set representing flaws in the object have a greater spatial correlation than data values representing grain noise in the 3D waveform data set.

A further aspect of the invention involves spatially and temporally sampling the object such that data values representing flaws in the object are correlated and data values representing grain noise in the object are substantially uncorrelated in the 3D waveform data set.

In accordance with one embodiment of the invention, the step of performing a 3D filtering operation includes filtering the 3D waveform data set with a 3×3×3 pixel filtering operation.

In accordance with another aspect of the invention, the step of converting the 3D waveform data set to a 3D filtered waveform data set includes using a $N_1 \times N_2 \times N_3$ filter size having spatial dimensions $N_1$ and $N_2$ that are each less than the flaw spatial correlation value and greater than the noise spatial correlation value of the 3D waveform data set, and having a temporal dimension $N_3$ that is less than the flaw temporal correlation value and greater than the noise temporal correlation value of the 3D waveform data set.

In accordance with yet another aspect of the invention, the step of scanning the object includes oversampling the object both spatially and temporally, in a manner which achieves a desired level of noise spatial and temporal correlations and flaw spatial and temporal correlations.

In a more particular embodiment of the invention, the step of oversampling the waveform signals includes sampling at a frequency which is greater than two and less than or equal to eleven times the ultrasonic frequency used in scanning the object.

In accordance with a preferred embodiment of the present invention, the step of converting the 3D waveform data set includes using a 3D median filtering operation to generate the 3D filtered waveform data set.

BRIEF DESCRIPTION OF THE DRAWINGS

Other objects and advantages of the subject invention will become apparent from a study of the following specification when viewed in light of the accompanying drawings, in which.

DETAILED DESCRIPTION OF THE PREFERRED EMBODIMENT

Figure 1:
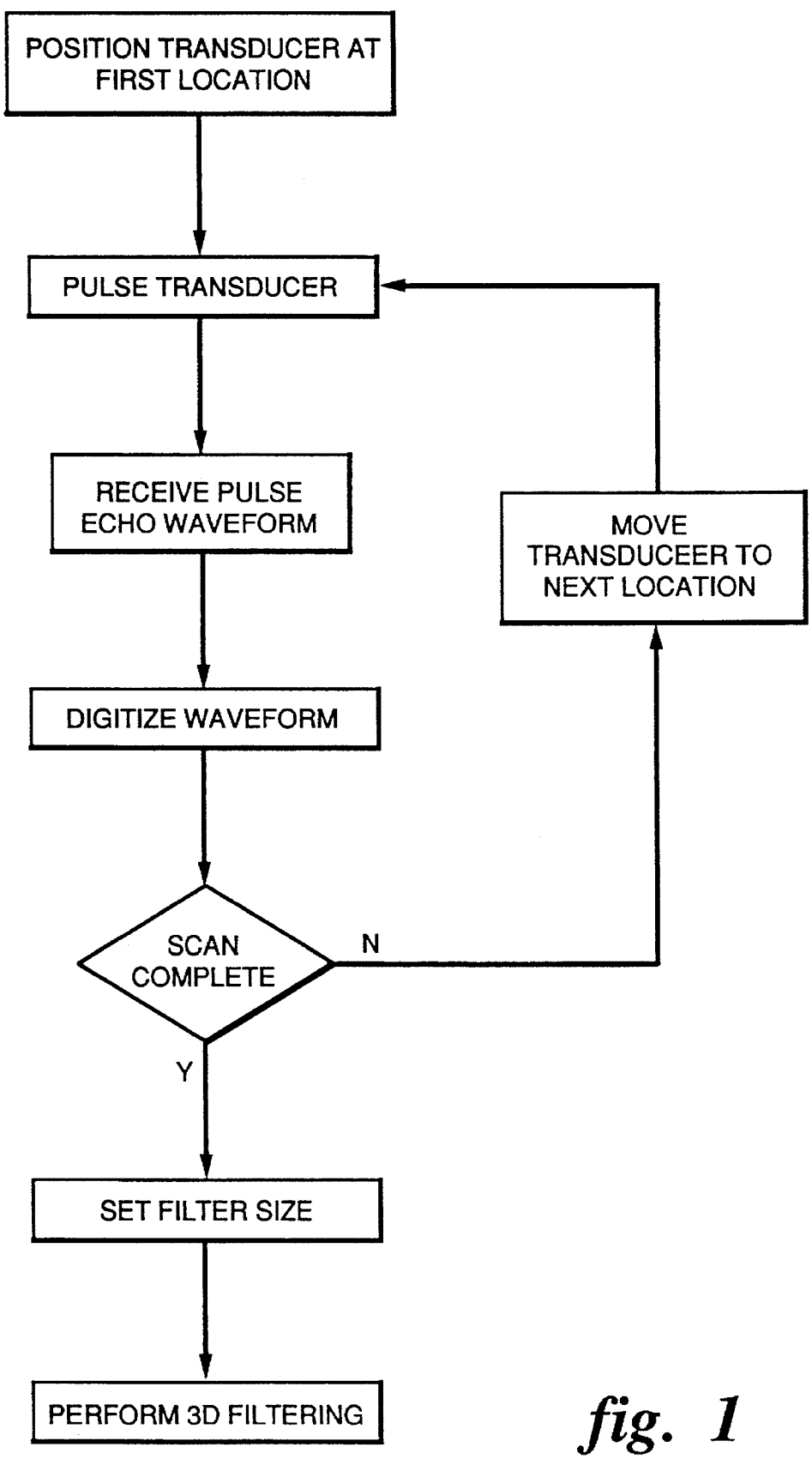
FIG. 1 is a flow chart of the steps which define a preferred embodiment of the grain noise suppression method of the present invention.
Figure 2:
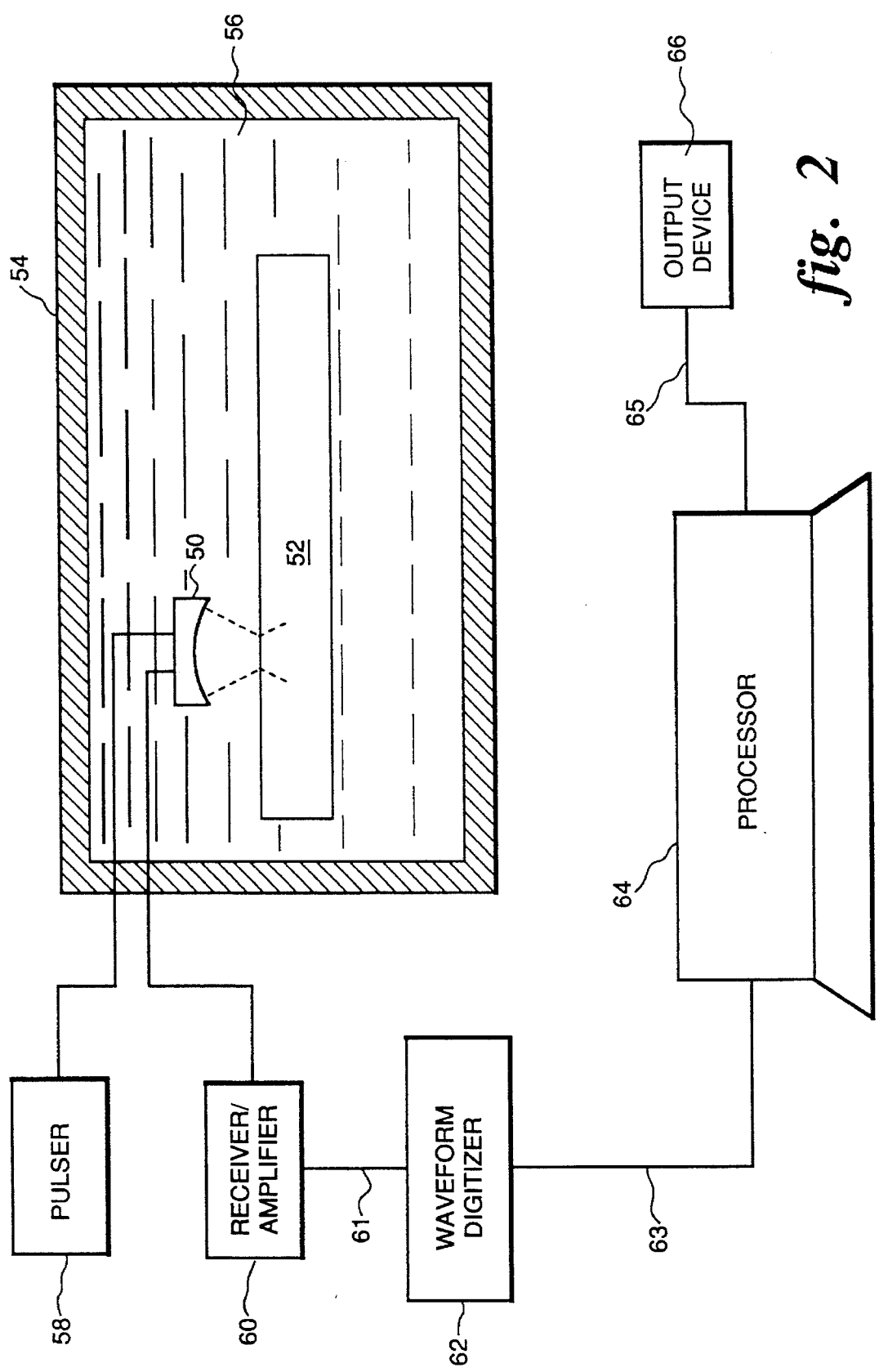
FIG. 2 depicts a preferred embodiment of the data acquisition system used in the method of the present invention.

Referring now to the drawings, and more particularly to FIGS. 1 and 2, the method of the present invention uses ultrasonic pulse echo inspection to scan an object at a plurality of locations (x,y) in an area of interest on the object to produce a three dimensional (3D) waveform data set which includes data representing a pulse echo waveform, or A-scan, for each scanned location (x,y) on the object. The present method has particularly utility in the inspection of metal objects or manufactured parts made of large grain metals such as titanium or the like, to identify indications such as actual flaws in the metal, abnormally large grains, or any other indications which are identifiable over the grain noise in the part, such as hard alpha defects or the like.

As shown in FIG. 2, the 3D waveform data set can be obtained by ultrasonic pulse echo inspection using an ultrasonic data acquisition system, wherein an ultrasonic transducer 50 is used to raster scan a part 52 with sound waves along a surface thereof. During the raster scan, the part 52 is immersed in a tank 54 full of liquid 56, such as water or the like. For each location of interest (x,y) on the part 52, the ultrasonic transducer 50 is pulsed by pulser 58 to send a sound wave through the part 52 which reflects off or echoes back signals from the part to the transducer 50. A receiver 60 is provided to receive and amplify the echo signals and transmit the signals to a waveform digitizer 62 via connection 61. The waveform digitizer 62 is operable to receive and convert the echo signals to digital data which represent the echo waveform, and to output the digitized data values to processor 64 via line 63. The data values, which represent an A-scan image for a particular location (x,y) are then stored in a data processor 64.

As shown in the flow chart of FIG. 1, the 3D waveform data set is obtained by initially positioning the transducer 50 at a first location (x,y) on the object 52, pulsing the transducer 50, receiving the pulse echo waveform therefrom, and digitizing the waveform, thereby obtaining a first A-scan corresponding to the first location (x,y). Next, the transducer 50 is moved to a second location (x,y) and an A-scan is obtained in the same manner as described above for the second location. This process is repeated until the scan is complete and an A-scan has been obtained for each location (x,y) of interest on the object. By moving the transducer 50 in both spatial directions x and y relative to the object and recording data representing an entire waveform at each location, a 3D waveform data set U(x,y,t) is obtained when the scan is complete which includes both spatial (x,y) and temporal (t) data values. This 3D waveform data set is known in the art as a T-scan or Z-scan. An output device 66, such as a video monitor or printer, coupled to the processor 64 via line 65 may be provided to enable the waveform data, or parts thereof, to be displayed or printed once generated. Inasmuch as ultrasonic pulse echo inspection is well known in the art, further particular details on obtaining a 3D waveform data set will not be further discussed herein.

Typically, ultrasound illuminated grains of the microstructure of an object have a larger spatial extent than the spatial extent of a flaw in the object. In accordance with the invention, the data acquisition system is preferably calibrated in a manner which takes advantage of the difference in spatial extent between ultrasound illuminated grains and flaws, as will be described in detail below.

In accordance with the invention, the object is preferably spatially scanned such that data values representing flaws in the 3D waveform data set have a greater spatial correlation than data values representing noise in the data set. Spatial correlation is the number of pixels in the image defined by the 3D data set at which a single flaw or grain noise can be identified. This is accomplished by moving the transducer during the scanning of the object by increments which are larger than the noise correlation distance and smaller than the flaw correlation distance. This increment is typically smaller than the spatial Nyquist rate, implying spatial oversampling. However, the particular flaw and noise spatial correlation which are used is a design parameter which can vary in accordance with the particular application in which the present method is used. The amount of oversampling chosen for a particular application involves, in part, a tradeoff between the size of the flaws one desires to detect and the amount of processing power required to process the data. All that is required by the present method is that the flaw spatial correlation be greater than the noise spatial correlation in the 3D waveform data set. The purpose for having a greater flaw spatial correlation will be explained in greater detail below.

In accordance with a preferred embodiment of the invention, the echo waveform produced at each location (x,y) is also oversampled in a manner which produces a greater flaw temporal correlation than noise temporal correlation in the 3D waveform data set. Temporal correlation is the number of data points in the data set along a single A-scan at which a flaw or grain can be identified. Temporal oversampling is achieved in the waveform digitizer 62 by sampling the waveform at a frequency which exceeds the Nyquist frequency. Similar to spatial oversampling, temporal oversampling is defined as sampling at a frequency which is above the theoretical minimum frequency at which a waveform can be resolved given by the Nyquist sampling theorem. In accordance with the Nyquist sampling theorem, the minimum sampling frequency at which a waveform can be resolved is twice the frequency of the transducer used to generate the waveform. This minimum frequency given by the Nyquist sampling theorem is known as two times carrier frequency. Thus, oversampling temporally is sampling the waveform at a frequency which is above the Nyquist rate or above two times carrier frequency. For example, if a 5 MHz transducer is used in the data acquisition system, temporal oversampling is sampling the waveform at greater than 10 MHz.

The waveform is preferably sampled at a frequency which causes data values representing flaws in the object to be correlated and data values representing grain noise in the object to be substantially uncorrelated along the individual A-scans. While in theory it is possible to temporally oversample the object such that the flaw temporal correlation is very high, it has been found that a flaw temporal correlation of between 3 and 11 is preferable for most applications. In other words, 3 to 11 adjacent points on an A-scan are preferably recorded which represent the same flaw in the object. It has further been found that a sampling frequency of 4 to 5 times carrier frequency will produce desirable results in many applications. However, the particular flaw temporal correlation which is obtained is a design parameter which can vary in accordance with the particular application in which the present method is used. All that is required by the present method is that the flaw temporal correlation be greater than the noise temporal correlation in the 3D waveform data set. The purpose for having a greater flaw temporal correlation in the 3D waveform data set will become clear from the description below.

Once a 3D waveform data set is obtained having given noise and flaw spatial correlations and noise and flaw temporal correlations, a 3D filtering operation is performed which converts the 3D waveform data set into a 3D filtered waveform data set, and which takes into account the differences in the flaw and noise correlations in a manner which smooths out the noise in the data set and leaves the flaw indications substantially unchanged.

The step of converting the 3D waveform data set into a 3D filtered waveform data set includes selecting a $N_1 \times N_2 \times N_3$ filter size preferably having spatial dimensions $N_1$ and $N_2$ that are each less than the flaw spatial correlation value and greater than the noise spatial correlation value of the 3D waveform data set. For example, if the noise spatial correlation is 1 (uncorrelated) and the flaw spatial correlation is 4, $N_1$ and $N_2$ are preferably selected to be between 1 and 4. Similarly, the temporal dimension $N_3$ is preferably selected such that it is greater than the noise temporal correlation value and less than the flaw temporal correlation value.

Inasmuch as the spatial correlation is typically the same in both the x and y dimensions, $N_1$ and $N_2$ are typically chosen to be equal to one another. The temporal dimension $N_3$ may have the same or a different value than the spatial dimensions $N_1$ and $N_2$ depending on the similarity or difference between the spatial and temporal correlations in the 3D waveform data set. Depending on the calibration of the data acquisition system used in scanning the object, the temporal and spatial correlations may be different, thus warranting a difference in the spatial and temporal dimensions of the 3D filter.

In order to achieve a maximum amount of smoothing of the noise data without smoothing the flaw data, each of the filter dimensions $N_1$, $N_2$ and $N_3$ are preferably selected to be the largest odd number which is less than the flaw correlation in each of the three data set dimensions, respectively. For example, if the flaw correlation in each dimension is determined to be 8, then the filter size is preferably selected to be 7×7×7. While even number filter dimensions can be used, they are not as convenient as odd number filters in that they cannot take into account the same number of data values on each side of the data value to be converted thereby.

If the filter size selected is larger than the flaw correlation, the filter will operate to smooth out the flaws as well as the noise. Conversely, if the filter size is too small it will not operate to smooth out the noise. Thus, an important aspect of the present invention is choosing the appropriate filter size for data collected from a given object by a data acquisition system having a given calibration, in accordance with the guidelines set forth above.

While the method of the present invention provides optimal results when the filter dimensions are selected such that they are the largest odd numbers between the noise and flaw correlation values in each dimension, respectively, it is not always necessary to determine beforehand the noise and flaw correlation values of the data set to be filtered. In accordance with the invention, it has been found that a 3×3×3 filter operation will provide desirable results in many applications, because this is the smallest odd number filter which can pickup a correlated flaw signal from uncorrelated noise in the data set. Thus, if the assumption can be made that noise is uncorrelated (correlation value of 1), then even without knowing the exact flaw correlation value, a 3×3×3 filter could be used to smooth the noise without smoothing the flaws in many data sets. If a 3×3×3 filter does not provide sufficient smoothing of the noise, the dimensions of the filter could be incrementally increased on a trial-and-error basis until the desired results are obtained. Even if some or all of the filter dimensions become slightly larger than the respective flaw correlation values, it may still provide some utility in some applications. Thus, predetermining the exact flaw correlation is not a required step in the method of the present invention.

The procedure for determining noise and flaw correlation values is well known in the art of signal processing and will not be explained in further detail herein.

Once the filter size is selected, the $N_1 \times N_2 \times N_3$ filter is used to convert the data value in the 3D waveform data set $U(x,y,t)$ into a 3D filtered waveform data set $V(x,y,t)$, wherein for each pixel value in $U(x,y,t)$ a filtered pixel value is obtained by taking into account the $N_1 \times N_2 \times N_3$ cube of data centered at that pixel. For example, if a 3×3×3 filter is used, each filtered data value in V(x,y,t) is determined by taking into account three data values on each of none adjacent digitized waveforms, thereby using 27 different data values from U(x,y,t) in calculating a filtered data value for V(x,y,t).

In accordance with the invention, the $N_1 \times N_2 \times N_3$ filter is preferably a 3D median filter which calculates the filtered data values V(x,y,t) to be the median value of the $N_1 \times N_2 \times N_3$ cube of data centered at each pixel in the 3D waveform data set U(x,y,t). If $N_1 = N_2 = N_3 = (2n+1)$, then $$V(x,y,t) = \text{median}(U(x-n:x+n, y-n:y+n, z-n:z+n))$$

Thus, if a 3×3×3 median filter is used, for each data value in the 3D waveform data set U(x,y,t) a corresponding filtered data value is calculated as the median data value of the 27 data values in the cube of data centered at that data value, thereby producing a 3D filtered waveform data set V(x,y,t).

While a 3D median filter is preferred because it reduces the effect of outlying data points and preserves the resolution of the data image, other filters can be used such as a mean, order-statistics which are close to the median, or any other suitable filter which enables smoothing of the noise data without substantially smoothing the flaw data. The actual statistic generated by the filter is a design parameter which can be selectively chosen depending on the particular application in which the present method is employed.

Figure 3A:
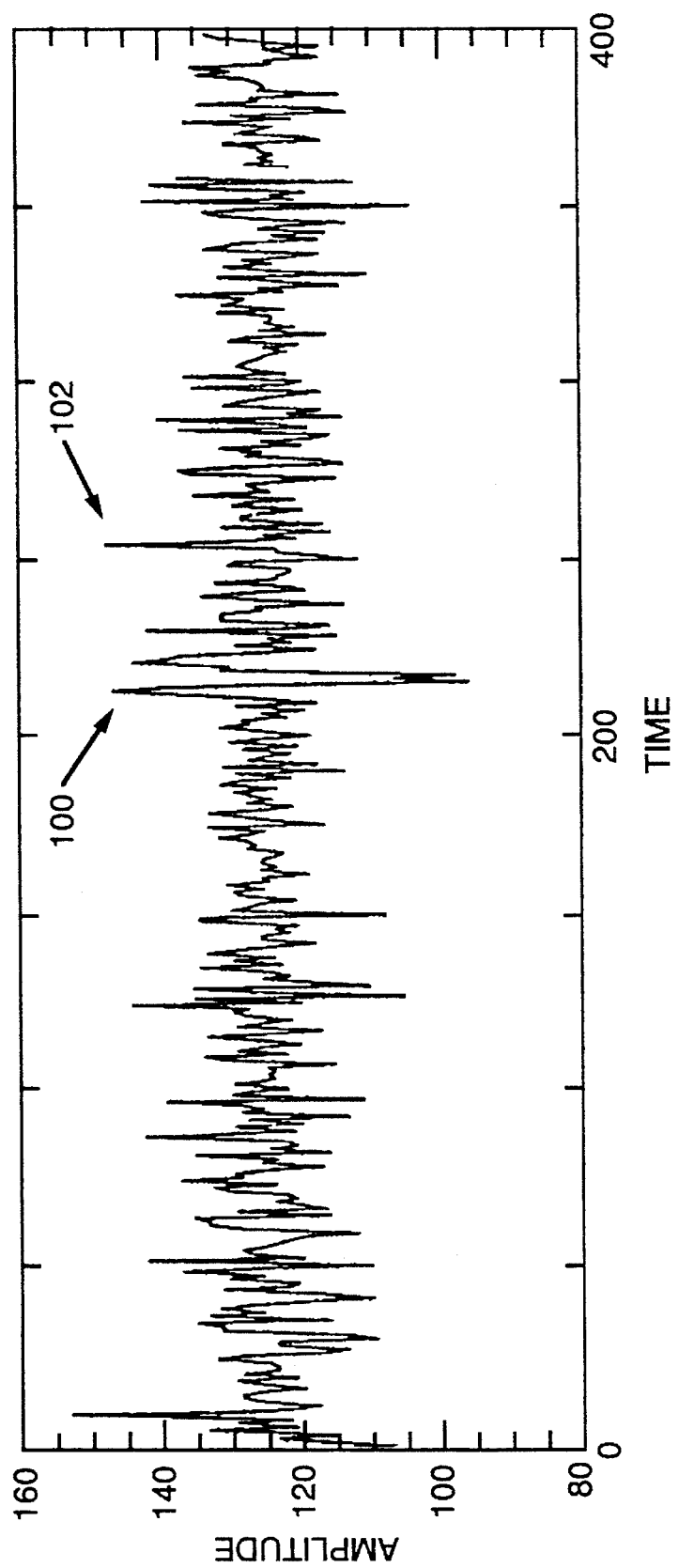
FIGS. 3a and 3b show an A-scan before and after the grain noise suppression method of the present invention has been applied thereto, respectively.
Figure 3B:
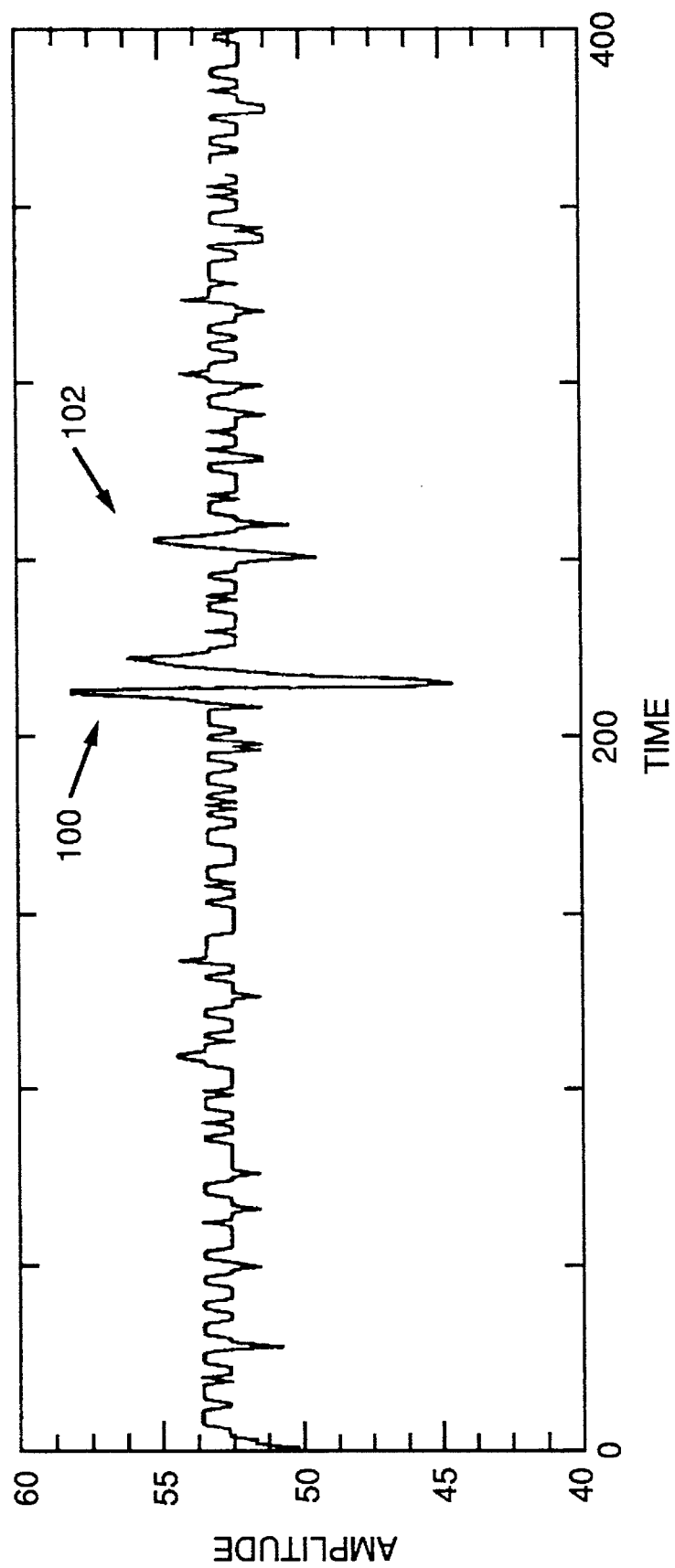

Referring now to the experimental results of FIGS. 3A and 3B, there is shown a single A-scan out of a 3D waveform data set before and after 3D filtering operation of the present invention was performed thereon, respectively. The front wall 100 and back wall 102 of a hard alpha inclusion representing a flaw are present in the waveform of FIG. 3A but they are not clearly visible because of grain noise also present therein. After performing a 3×3×3 median filtering operation on each pixel of the waveform of FIG. 3A, the filtered waveform of FIG. 3B was produced in which the two phase reversed echoes from the front wall 100 and back wall 102 of the hard alpha inclusion are now clearly visible. Generally, grain noise has been reduced in waveform data by a factor of two to three using the method of the present invention.

Thus, the present invention provides a flexible and reliable method for suppressing grain noise relative to flaw indications in ultrasonic inspection which takes advantage of the difference in spatial and temporal correlations between grain noise and flaw indications, thereby enabling flaws to be more accurately identified.

As can be seen from the foregoing description, the present method provides an increased probability of flaw detection and a decreased probability of false flaw indications compared to that which has heretofore been achieved by prior art techniques.

While several aspects and embodiments of the invention have been illustrated and described, it will be apparent to those of ordinary skill in the art that various changes and modifications may be made without deviating from the inventive concepts and spirit of the invention, and it is intended by the appended claims to define all such concepts which come within the full scope and true spirit of the invention.

What is claimed is:

1. A method of ultrasonically inspecting a metal object formed from a plurality of grains wherein grain noise arises at interfaces between the plurality of grains during the ultrasonic inspection of the metal object, the method comprising the steps of:

ultrasonically scanning the metal object with sound wave energy;

detecting waveform signals reflected from the metal object;

determining data values from said waveform signals which define a 3D waveform data set U(x,y,t) having both spatial (x,y) and temporal (t) ultrasonic data values which map directly to a third spatial dimension from the scanned metal object, the 3D waveform data set U(x,y,t) corresponds to a 3D volumetric region in the metal object;

converting the 3D waveform data set U(x,y,t) into a 3D filtered waveform data set V(x,y,t) by performing a 3D filtering operation thereon, wherein for each data value in said 3D waveform data set U(x,y,t), a filtered data value is obtained by taking into account data values which are adjacent in 3D space;

suppressing grain noise arising at the interfaces between the plurality of grains within the metal object with the 3D filtered waveform data set V(x,y,t); and generating a full volume 3D image of the 3D filtered waveform data set V(x,y,t).

2. The method as defined in claim 1, wherein the step of scanning the object includes spatially sampling the object such that data values in the 3D waveform data set U(x,y,t) representing flaws in the object have a greater spatial correlation than data values representing grain noise in the 3D waveform data set.

3. The method as defined in claim 1, wherein the step of determining data values includes sampling said waveform signals such that data values in the 3D waveform data set representing flaws in the object have greater temporal correlation than data values representing grain noise in the 3D waveform data set.

4. The method as defined in claim 2, wherein the step of determining data values includes sampling said waveform signals such that data values in the 3D waveform data set representing flaws in the object have greater temporal correlation than data values representing grain noise in the 3D waveform data set.

5. The method as defined in claim 4, wherein the step of spatially sampling the object includes sampling the object such that data values representing flaws are correlated and data values representing grain noise are substantially uncorrelated in the 3D waveform data set.

6. The method as defined in claim 4, wherein the step of sampling said waveform signals includes sampling such that data values representing flaws in the object are correlated and data values representing grain noise are substantially uncorrelated in the 3D waveform data set.

7. The method as defined in claim 5, wherein the step of sampling said waveform signals includes sampling such that data values representing flaws in the object are correlated and data values representing grain noise are substantially uncorrelated in the 3D waveform data set.

8. The method as defined in claim 7, wherein said step of performing a 3D filtering operation includes filtering said 3D waveform data set with a 3×3×3 pixel filter operation.

9. The method as defined in claim 7, wherein said 3D waveform data set has a flaw spatial correlation value and a noise spatial correlation value, and further wherein said step of converting said 3D waveform data set to a 3D filtered waveform data set includes using a $N_1 \times N_2 \times N_3$ filter size having spatial dimensions $N_1$ and $N_2$ that are each less than the flaw spatial correlation value and greater than the noise spatial correlation value of the 3D waveform data set.

10. The method as defined in claim 4, wherein said 3D waveform data set has a flaw temporal correlation value and a noise temporal correlation value, and further wherein said step of converting said 3D waveform data set to a 3D filtered waveform data set includes selecting a $N_1 \times N_2 \times N_3$ filter size having a temporal dimension $N_3$ that is less than the flaw temporal correlation value and greater than the noise temporal correlation value.

11. The method as defined in claim 9, wherein said 3D waveform data set has a flaw temporal correlation value and a noise temporal correlation value, and further wherein said step of converting said 3D waveform data set to a 3D filtered waveform data set includes selecting a $N_1 \times N_2 \times N_3$ filter size having a temporal dimension $N_3$ that is less than the flaw temporal correlation value and greater than the noise temporal correlation value.

12. The method as defined in claim 11, wherein said step of selecting a $N_1 \times N_2 \times N_3$ filter size includes selecting said spatial dimensions $N_1$ and $N_2$ to be equivalent.

13. The method as defined in claim 12, wherein said step of selecting a $N_1 \times N_2 \times N_3$ filter size includes selecting said temporal dimensions $N_3$ to be equivalent to said spatial dimensions $N_1$ and $N_2$.

14. The method as defined in claim 12, wherein said step of selecting said temporal dimension $N_3$ includes selecting said temporal dimensions $N_3$ to be different than said spatial dimensions $N_1$ and $N_2$.

15. The method as defined in claim 9, wherein said step of selecting a $N_1 \times N_2 \times N_3$ filter size includes selecting $N_1$, $N_2$ and $N_3$ to be odd numbers.

16. The method as defined in claim 2, wherein said step of spatially sampling the object includes oversampling the object spatially.

17. The method as defined in claim 4, wherein said step of spatially sampling the object includes oversampling the object spatially.

18. The method as defined in claim 3, wherein said step of sampling said waveform signals includes temporally oversampling said waveform signals.

19. The method as defined in claim 4, wherein said step of sampling said waveform signals includes temporally oversampling said waveform signals.

20. The method as defined in claim 18, wherein said step of oversampling said waveform signals includes sampling at a frequency which is greater than two and less than or equal to eleven times an ultrasonic frequency used in scanning the object.

21. The method as defined in claim 19, wherein said step of oversampling said waveform signals includes sampling at a frequency which is greater than two and less than or equal to eleven times an ultrasonic frequency used in scanning the object.

22. The method as defined in claim 1, wherein said step of converting said 3D waveform data set includes using a 3D median filtering operation.

23. The method as defined in claim 4, wherein said step of converting said 3D waveform data set includes using a 3D median filtering operation.

24. The method as defined in claim 1, wherein said step of converting said 3D waveform data set includes using a 3×3×3 median filtering operation.

25. The method as defined in claim 8, wherein said step of converting said 3D waveform data set includes using a 3×3×3 median filtering operation.

26. The method as defined in claim 1, wherein said step of converting said 3D waveform data set includes using a 3D mean filtering operation.

27. The method as defined in claim 4, wherein said step of converting said 3D waveform data set includes using a 3D mean filtering operation.

28. The method of claim 1, wherein said step of converting said 3D waveform data set includes using a 3×3×3 mean filtering operation.

29. The method as defined in claim 8, wherein said step of converting said 3D waveform data set includes using a 3×3×3 mean filtering operation.

30. The method as defined in claim 11, wherein said step of selecting a $N_1 \times N_2 \times N_3$ filter size includes selecting $N_1$ and $N_2$ to be the largest odd number which is less than the flaw spatial correlation value, and selecting $N_3$ to be the largest odd number which is less than the flaw temporal correlation value.

31. The method as defined in claim 18, wherein said step of oversampling said waveform signals includes sampling at a frequency with three to four times an ultrasonic frequency used in scanning the object.

* * * * *